United States Patent [19]

Harris et al.

[11] Patent Number: 5,374,442
[45] Date of Patent: Dec. 20, 1994

[54] METHOD OF PREPARING REDUCED FAT FOODS

[75] Inventors: Donald W. Harris; Jeanette A. Little, both of Decatur, Ill.

[73] Assignee: A. E. Staley Manufacturing Company, Decatur, Ill.

[21] Appl. No.: 19,162

[22] Filed: Feb. 16, 1993

Related U.S. Application Data

[63] Continuation-in-part of Ser. No. 918,862, Jul. 30, 1992, and a continuation-in-part of Ser. No. 908,728, Jul. 6, 1992, which is a continuation of Ser. No. 578,994, Sep. 6, 1990, abandoned, which is a continuation-in-part of Ser. No. 483,208, Feb. 20, 1990, abandoned, said Ser. No. 918,862, is a continuation-in-part of Ser. No. 746,381, Aug. 16, 1991, abandoned, and a continuation-in-part of Ser. No. 798,291, Nov. 26, 1991, abandoned.

[51] Int. Cl.$^5$ .................................. A23L 1/05
[52] U.S. Cl. .......................... 426/573; 426/549; 426/661; 426/804
[58] Field of Search ............ 426/661, 573, 578, 658, 426/603, 604, 804, 549; 127/29, 32, 33, 36, 88, 39, 40, 58, 65, 69–71; 252/315.3

[56] References Cited

U.S. PATENT DOCUMENTS

| | | | |
|---|---|---|---|
| 675,822 | 6/1901 | Duryea | 127/33 |
| 696,949 | 4/1902 | Duryea | 127/33 |
| 2,068,051 | 1/1937 | Canton | 426/578 |
| 2,131,064 | 9/1938 | Musher | 426/633 |
| 2,503,053 | 4/1950 | Kerr | 127/38 |
| 2,791,508 | 5/1957 | Rivoche | 426/573 |
| 2,805,995 | 9/1957 | Adelson | 252/33.6 |
| 2,978,446 | 4/1961 | Battista | 260/212 |
| 3,023,104 | 2/1962 | Battista | 99/1 |
| 3,067,067 | 12/1962 | Etheridge | 127/71 |
| 3,093,486 | 6/1963 | Krett | 99/144 |
| 3,133,836 | 5/1964 | Winfrey | 127/71 |
| 3,197,337 | 7/1965 | Schink | 127/28 |
| 3,219,483 | 11/1965 | Goos | 127/28 |
| 3,351,489 | 11/1967 | Battista | 127/32 |
| 3,532,602 | 10/1970 | Seidman | 195/31 |
| 3,556,942 | 1/1972 | Hathaway | 195/31 |
| 3,582,359 | 6/1971 | Horn | 426/573 |
| 3,586,536 | 6/1971 | Germino | 127/32 |
| 3,600,186 | 8/1971 | Mattson | 99/1 |
| 3,632,475 | 1/1972 | Sugimoto et al. | 127/71 X |
| 3,666,557 | 5/1972 | Jensen | 127/32 |
| 3,671,269 | 6/1972 | Germino | 99/139 |
| 3,705,811 | 12/1972 | Yoshida | 99/91 |
| 3,717,475 | 2/1973 | Germino | 99/134 |
| 3,730,840 | 5/1973 | Sugimoto | 195/31 R |
| 3,830,697 | 8/1974 | Yoshida | 195/31 R |
| 3,879,212 | 4/1975 | Yoshida | 106/213 |
| 3,881,991 | 5/1975 | Kurimoto | 195/31 |
| 3,883,365 | 5/1975 | Forsberg | 127/60 |
| 3,928,062 | 12/1975 | Yamauchi | 127/60 |
| 3,962,465 | 6/1976 | Richter | 127/48 |
| 3,986,890 | 10/1976 | Richter | 127/38 |
| 4,009,291 | 2/1977 | Mitchell | 426/548 |
| 4,069,157 | 1/1978 | Hoover | 210/433 M |
| 4,143,163 | 3/1979 | Hutchison | 426/96 |
| 4,143,174 | 3/1970 | Shah | 426/570 |
| 4,192,900 | 3/1980 | Cheng | 426/578 |
| 4,199,374 | 4/1980 | Dwivedi | 127/60 |
| 4,209,503 | 6/1980 | Shah | 424/49 |

(List continued on next page.)

FOREIGN PATENT DOCUMENTS 1016006 8/1977 Canada .

(List continued on next page.)

OTHER PUBLICATIONS

Allmere et al., Derwent Abstract 93-174080 for SU 1736975, Jun. 1989.

(List continued on next page.)

*Primary Examiner*—Donald E. Czaja
*Assistant Examiner*—Leslie Wong
*Attorney, Agent, or Firm*—Arnold, White & Durkee

[57] ABSTRACT

A method of preparing reduced fat foods is provided which employs a recrystallized and fragmented amylose precipitate. A starch having both amylose and amylopectin is gelatinized to allow preparation of pure amylose as a permeate of membrane foltration. the amylose is precipitated, recrystallized and then fragmented to form an aqueous dispersion that is useful in replacing fat in a variety of food formulations. The amylose precipitate can be derived from a starch which contains amylose, e.g. common corn starch, by gelatinizing the starch followed by precipitation of the amylose separation.

7 Claims, No Drawings

U.S. PATENT DOCUMENTS

| | | | |
|---|---|---|---|
| 4,263,334 | 4/1981 | McGinley | 426/573 |
| 4,276,312 | 6/1981 | Merritt | 426/96 |
| 4,291,065 | 9/1981 | Zobel | 426/549 |
| 4,305,964 | 12/1981 | Moran | 426/99 |
| 4,308,294 | 12/1981 | Rispoli | 426/564 |
| 4,423,084 | 12/1982 | Trainor | 426/589 |
| 4,477,480 | 10/1984 | Seidel | 426/578 |
| 4,492,714 | 1/1985 | Cooper | 426/602 |
| 4,510,166 | 4/1985 | Lenchin | 426/565 |
| 4,533,354 | 8/1985 | Cook | 366/176 |
| 4,536,408 | 8/1985 | Morehouse | 426/250 |
| 4,551,177 | 11/1985 | Trubiano | 106/210 |
| 4,560,559 | 12/1985 | Ottenburg | 426/19 |
| 4,587,131 | 5/1986 | Bodor | 426/603 |
| 4,591,507 | 5/1986 | Bodor | 426/604 |
| 4,643,773 | 2/1987 | Day | 127/30 |
| 4,670,272 | 6/1987 | Chen | 426/573 |
| 4,726,957 | 2/1988 | Lacourse | 426/578 |
| 4,728,526 | 3/1988 | Avera | 426/633 |
| 4,744,987 | 5/1988 | Mehra | 424/156 |
| 4,761,292 | 8/1988 | Augustine | 426/321 |
| 4,787,939 | 11/1989 | Barker | 127/37 |
| 4,810,307 | 3/1989 | Caton | 127/63 |
| 4,810,646 | 3/1989 | Jamas | 435/101 |
| 4,814,195 | 3/1989 | Yokohama | 426/633 |
| 4,828,868 | 5/1989 | Lasdon | 426/633 |
| 4,832,977 | 5/1989 | Avera | 426/633 |
| 4,859,484 | 8/1989 | Bielskis | 426/96 |
| 4,869,919 | 9/1989 | Lowery | 426/604 |
| 4,885,180 | 12/1989 | Cochran | 426/241 |
| 4,886,678 | 12/1989 | Chiu | 426/578 |
| 4,911,946 | 3/1990 | Singer | 426/658 |
| 4,917,915 | 4/1990 | Cain | 426/573 |
| 4,937,091 | 6/1990 | Zallie | 426/582 |
| 4,942,055 | 7/1990 | Avera | 426/633 |
| 4,948,615 | 8/1990 | Zallie | 426/573 |
| 4,954,178 | 9/1990 | Caton | 127/32 |
| 4,957,750 | 9/1990 | Cochran | 426/19 |
| 4,962,094 | 10/1990 | Jamas | 514/54 |
| 4,971,723 | 11/1990 | Chiu | 252/315.3 |
| 4,981,709 | 1/1991 | Furcsik | 426/565 |
| 4,988,531 | 1/1991 | Moore | 426/578 |
| 4,990,355 | 2/1991 | Gupta | 426/602 |
| 5,034,240 | 7/1991 | Tanaka | 426/607 |
| 5,035,904 | 7/1991 | Huang | 426/243 |
| 5,037,929 | 8/1991 | Rajagopalan | 426/578 |
| 5,051,271 | 9/1991 | Iyengar | 426/658 |
| 5,094,872 | 3/1992 | Furcsik | 426/578 |
| 5,104,674 | 4/1992 | Chen | 426/573 |
| 5,106,644 | 4/1992 | El-Nokaly | 426/603 |
| 5,110,612 | 5/1992 | Quarles | 426/573 |
| 5,131,953 | 7/1992 | Kasica | 127/65 |
| 5,137,742 | 8/1992 | Bakal | 426/589 |
| 5,147,665 | 9/1992 | Furcsik | 426/19 |
| 5,192,569 | 3/1993 | McGinley et al. | 426/96 |

FOREIGN PATENT DOCUMENTS

| | | |
|---|---|---|
| 0052899 | 2/1982 | European Pat. Off. |
| 0237120 | 9/1987 | European Pat. Off. |
| 0298561 | 1/1989 | European Pat. Off. |
| 0327120 | 8/1989 | European Pat. Off. |
| 0327288 | 8/1989 | European Pat. Off. |
| 0340035 | 11/1989 | European Pat. Off. |
| 0367064 | 5/1990 | European Pat. Off. |
| 0372184 | 6/1990 | European Pat. Off. |
| 0387940 | 9/1990 | European Pat. Off. |
| 0420314 | 4/1991 | European Pat. Off. |
| 0420315 | 4/1991 | European Pat. Off. |
| 0427312 | 5/1991 | European Pat. Off. |
| 0430329 | 6/1991 | European Pat. Off. |
| 0443844 | 8/1991 | European Pat. Off. |
| 0470870 | 2/1992 | European Pat. Off. |
| 0480433 | 4/1992 | European Pat. Off. |
| 0486936 | 5/1992 | European Pat. Off. |
| 142646A | 7/1980 | German Dem. Rep. |
| 161178A | 5/1985 | German Dem. Rep. |
| 110957 | of 1897 | Germany |
| 60-160833 | 8/1985 | Japan |

(List continued on next page.)

OTHER PUBLICATIONS

"Avicel RC in canned foods", bulletin No. RC-31, FMC Corp. (May 1972).

"Avicel microcrystalline cellulose; the non-caloric ingredient", bulletin, American Viscose Corp.

"Avicel RC 581 Technical Bulletin", bulletin No. RC-11, FMC Corp., 11/69-1M.

"Avicel RC-591 in foods", bulletin No. RC-22, FMC Corp. (May 1971).

"Avicel RC in bakery products", bulletin No. RC-35, FMC Corp.

(List continued on next page.)

FOREIGN PATENT DOCUMENTS

| | | |
|---|---|---|
| 3-296501 | 12/1991 | Japan . |
| 4-46901 | 2/1992 | Japan . |
| 2247242 | 2/1992 | United Kingdom . |
| WO87/04465 | 7/1987 | WIPO . |
| WO89/12403 | 12/1989 | WIPO . |
| WO90/00010 | 1/1990 | WIPO . |
| WO90/06343 | 6/1990 | WIPO . |
| WO90/15147 | 12/1990 | WIPO . |
| WO91/01091 | 2/1991 | WIPO . |
| WO91/01092 | 2/1991 | WIPO . |
| WO91/07106 | 5/1991 | WIPO . |
| WO91/12728 | 9/1991 | WIPO . |
| WO92/02614 | 2/1992 | WIPO . |
| WO92/21703 | 12/1992 | WIPO . |

OTHER PUBLICATIONS

"Avicel pricing", bulletin, American Viscose Corp. (Jan. 1961).

"C9-112 microcrystalline starch", bulletin, A. E. Staley Mfg. Co. (Jan. 1972), with notes by A. H. Young.

"Food Labelling: definitions of the terms cholesterol free, low cholesterol, and reduced cholesterol", 55 Fed. Reg. 29456 (1990).

"Food labelling: serving sizes", 55 Fed. Reg. 29517 (1990).

"Low fat ground beef patties", brochure, A. E. Staley Mfg. Co. (Oct. 1991).

"Low-fat pork sausage patty", formula sheet CHSF7 196211, A. E. Staley Mfg. Co.

"Nepol Amylose", market development bulletin No. 101, A. E. Staley Mfg. Co. (1962).

"New generation of foods with reduced fat", Food Engineering, pp. 23–26 (Jan. 1990).

"Paselli SA2; the natural alternative to fats and oils", product bulletin, AVEBE b.a., Foxhol., Holland, ref. No. 05.12.31.167 EE (Jun. 1988).

"RANNIE High Pressure Laboratory Homogenizer", service manual, Rannie a/s, Roholmsvej 8, DK-2620, Denmark (1988).

"Reduced oil salad dressing", technical publication, A. E. Staley Mfg. Co.

"Solve tough process filtration problems with Ceraflo ceramic systems", technical bulletin, lit. No. SD113, Feb. 1989 89-418, Millipore Corp. (1989).

"STA-SLIM starches", technical data sheet, TDS 507 096060, A. E. Staley Mfg. Co.

"Staley Formulation of Food Starch-Modified", new product review presented to U.S. Food and Drug Administration by A. E. Staley Mfg. Co. (Nov. 1990).

"STELLAR Fat Replacer, Structure", technical information bulletin, A. E. Staley Mfg. Co., TIB 29 195060 (Jun. 1991).

"STELLAR Fat Replacer", technical data sheet, A. E. Mfg. Co. TDS 513 192250 (Jun. 1991).

"STELLAR Fat Replacer, Handling, Storage, and Preparation", technical information bulletin, A. E. Staley Mfg. Co., TIB 28 195060 (Jun. 1991).

Ambler, "Centrifugation", Handbook of Separation Techniques for Chemical Engineers, pp. 4-60 to 4-88 (McGraw Hill 1988).

Applewhite, "Fats and fatty oils", Encyclopedia of Chemical Technology, vol. 9, pp. 795–831 (Kirk-Othmer, eds., John Wiley & Sons 1980).

Atwell et al, "Characterization of quinoa starch", Cereal Chemistry, vol. 60, pp. 9–11 (1983).

Battista et al, "Colloidal macromolecular phenomena. Part II. Novel microcrystals of polymers", Journal of Applied Polymer Science, vol. 11, pp. 481–498 (1967).

Battista et al, "Microcrystalline cellulose", Industrial and Engineering Chemistry, vol. 54, pp. 20–29 (1962).

BeMiller, "Gums", Encyclopedia of Food Science & Technology, vol. 2, pp. 1338–1344 (John Wiley & Sons 1992).

Bouchard et al, "High performance liquid chromatographic monitoring of carbohydrate fractions in partially hydrolyzed corn starch", J. Agric. Food Chem., vol. 36, pp. 1188–1192 (1988).

Dickinson, "Particle gels", Chemistry & Industry. pp. 595–599 (Oct. 1990).

Dillon, "Gums and starches bulk up low-cal foods", Food Engineering (Jan. 1990).

Duxbury, "Modified food starches partially replace fats, oils & provide smooth texture", Food Processing, pp. 86–88 (Nov. 1990).

Duxbury, "Pre-hydrated gums eliminate lumping, long hydration times," Food Processing, pp. 44–48 (Jun. 1992).

Duxbury, "Fat-sparing starch can replace 100% fat/oil for 96% caloric reduction", Food Processing, p. 38 (Dec. 1990).

Dziezak, "Emulsifiers: the interfacial key to emulsion stability", Food Technology, vol. 42, No. 10, pp. 171–186 (Oct. 1988).

(List continued on next page.)

OTHER PUBLICATIONS

Dziezak, "Mambrane separation technology offers processors unlimited potential", Food Technology, pp. 108–113 (Sep. 1990).

Erdi et al, "Rheological characteristics of polymeric microcrystal-gels", Journal of Colloid and Interface Science, vol. 28, pp. 36–47 (1968).

Falkiewicz, "Avicel in suspensions—dispersion, rheology and colloid science", Soap, Cosmetics, Chemical Specialties, pp. 27–34 (Apr. 1979).

Faulkner et al, "Size reduction", Encyclopedia of Chemical Technology, vol. 21, pp. 132–162 (Kirk Othmer eds., John Wiley & Sons, 1983).

Ghiasi et al, "Effects of flour components and dough ingredients on starch gelatinization", Cereal Chemistry, vol. 60, No. 1, pp. 58–61 (1983).

Giese, "Developing low-fat meat products", Food Technology, pp. 100–108 (Apr. 1992).

Griffin, "Emulsions", Encyclopedia of Chemical Technology, vol. 8, pp. 900–930 (Kirk-Othmer, eds., John Wiley & Sons, 3d ed 1979).

Jane et al, "Structure studies of amylose-V complexes and retrograded amylose by action of alpha amylases, and a new method for preparing amylodextrins", Carbohydrate Research, vol. 132, pp. 105–118 (1984).

Jane et al, "Preparation and properties of small particle corn starch", Cereal Chemistry, vol. 69, pp. 280–283 (1992).

Kerr, Chemistry and Industry of Starch, 2d ed., pp. 564–567 (Academic Press 1950).

Klinkowski, "Ultrafiltration", Encyclopedia of Chemical Technology, vol. 23, pp. 439–461 (Kirk-Othmer, eds., John Wiley & Sons, 3d ed. 1983).

Knightly, "The evolution of softeners and conditioners used in baked foods", The Bakers Digest, pp. 64–75 (Oct. 1973).

Koizumi et al, "High performance anion-exchange chromatography of homogenous D-gluco oligosaccharides and polysaccharides (polymerization degree equal to or greater than 50) with pulsed amphoteric detection", Journal of Chromatography, vol. 46, pp. 365–373 (1989).

Krog, "Functions of emulsifiers in food systems", J. Am. Oil Chemists' Society, vol. 54, pp. 124–131 (1978).

Lansky et al, "Properties of the fractions and linear subfractions from various starches", vol. 71, pp. 4066–4075 (1949).

Larsson et al, "Annealing of starch at an intermediate water content", Starch/Starke, vol. 43, No. 6, pp. 227–231 (Jun. 1991).

Lavanchy et al., "Centrifugal separation", Encyclopedia of Chemical Technology, vol. 5, pp. 194–233 (Kirk-Othmer, eds., John Wiley & Sons, 3d ed., 1979).

Luu et al, "Model structure for liquid water, etc.", Travaux de la Societe de Pharmacie de Montpellier, vol. 41, No. 3, pp. 203–212 (1981).

Manley, Technology of Biscuits, Crackers and Cookies, pp. 335–347 (Ellis Horwood 1983).

Mason, "Chemistry with ultrasound", Critical Reports on Applied Chemistry, vol. 28, pp. 1–26, 91–98, 159–187 (Elsevier Science Publishers 1990).

Matthews, Legumes: Chemistry, Technology, and Human Nutrition, pp. 226–229 (Marcel Dekker 1989).

Matz, Cookie and Cracker Technology, pp. 163–167 (AVI Publishing 1968).

Mussulman et al, "Electron microscopy of unmodified and acid-modified corn starches", Cereal Chemistry, vol. 45, pp. 162–171 (1968).

Nara et al, "Study on relative crystallinity of moist potato starch", Starke/Starch, vol. 30, pp. 111–114 (1978).

Orr, "Size measurement of particles", Encyclopedia of Chemical Technology, vol. 21, pp. 106–131 (Kirk Othmer eds., John Wiley & Sons, 1983).

Pancoast et al, Handbook of Sugars, pp. 157–287 (AVI Publishing 1980).

Patterson, Hydrogenation of Fats and Oils, pp. 44–48, 173–182, 291–304 (Applied Science Publishers, 1983).

Paul et al, "Membrane technology", Encyclopedia of Chemical Technology, vol. 15, pp.92–131 (Kirk-Othmer, eds., John Wiley & Sons, 3d ed. 1981).

Pszczola, "Oat-bran-based ingredient blend replaces fat in ground beef and pork sausage", Food Technology, pp. 60–66 (Nov. 1991).

Rees et al, "Homogenizers", Encyclopedia of Foods Engineering, pp. 467–472 (Hall et al eds., AVI Publ. 1986).

Reuter, "Homogenization", Encyclopedia of Food Science, pp. 374–376 (Peterson et al eds., AVI Publ. Co., 1978).

Reuther et al, "Structure of maltodextrin gels—a small angle X-ray scattering study", Colloid and Polymer Science, vol. 261, pp. 271–276 (1983).

(List continued on next page.)

OTHER PUBLICATIONS

Richards, Breads, Rolls and Sweet Doughs, pp. 92–95 (Peacock Business Press, 1973).

Richardson, "Molecular mobilities of instant starch gels determined by oxygen-17 and carbon-14 nuclear magnetic resonance", Journal of Food Science, vol. 53, pp. 1175–1180 (1988).

Russell et al, "Characterization of resistant starch from wheat and maize", Journal of Cereal Science, vol. 9, pp. 1–15 (1989).

Sanderson, "Polysaccharides in foods", Food Technology, pp. 50–57 and 83 (Jul. 1981).

Savage et al, "Effects of certain sugars and sugar alcohols on the swelling of cornstarch granules", Cereal Chemistry, vol. 55, No. 4, pp. 447–454 (1978).

Shannon et al, "Genetics and physiology of starch development", Starch: Chemistry and Technology, pp. 25–35 (Whistler et al eds., Academic Press 1984).

Sievert et al, "Enzyme resistant starch. I. Characterization and evaluation of enzymatic, thermoanalytical, and microscopic methods", Cereal Chemistry, vol. 66, pp. 342–347 (1989).

Spies et al, "Effect of sugars on starch gelatinization", Cereal Chemistry, vol. 59, No. 2, pp. 128–131 (1982).

Stadelman et al, Egg and Poultry Meat Processing, pp. 52–63 (Ellis Horwood 1988).

Stute, "Hydrothermal modification of starches: the difference between annealing and heat/moisture-treatment", Starch/Stärke, vol. 44, pp. 205–214 (1992).

Swientek, "'Microfluidizing' technology enhances emulsion stability", Food Processing, pp. 152–153 (Jun.1990).

Taki, "Functional ingredient blend produces low-fat meat products to meet consumer expectations", Food Technology, pp. 70–74 (Nov. 1991).

Teot, "Resins, water-soluble", Encyclopedia of Chemical Technology, vol. 20, pp. 207–230 (John Wiley & Sons 1982).

Trout, "Pasteurization", Encyclopedia of Food Science, pp. 600–604 (Peterson et al eds., AVI Publ. Co., 1978).

Wang, "Meat processing I", Encyclopedia of Food Engineering, pp. 545–557 (AVI Publishing 1986).

Whistler et al, "Effect of acid hydrolysis on the retrogradation of amylose", Cereal Chemistry, vol. 25, No. 6, pp. 418–424 (1948).

White et al, "Predicting gelatinization temperatures of starch/sweetener systems for cake formulations by differential scanning calorimetry. I. Development of model." Cereal Foods World, vol. 35, No. 8, pp. 728–731 (Aug. 1990).

Wilhoft, "Recent developments on the bread staling problem", The Bakers Digest, pp. 14–20 (Dec. 1973).

Wurzburg, Modified Starches: Properties and Uses, pp. 18–23, 38–40, 244–245, and 251–252 (CRC Press, 1986).

Yamaguchi et al, "Electron microscopic observations of waxy maize starch", Journal of Ultrastructure Research, vol. 69, pp. 249–261 (1979).

Young, "Evaluation of microcrystals prepared from MIRA-QUIK C in the pilot plant spray dried in the presence of sodium carboxymethylcellulose (C9–112)", project report No. RD 73-17, A. E. Staley Mfg. Co. (Apr. 1973).

Tegge, "Produkte der sauren Stärkehydrolyse", Die Stärken, pp. 244–246 (1981). (English translation).

METHOD OF PREPARING REDUCED FAT FOODS

CROSS-REFERENCE TO RELATED APPLICATIONS

This application is a continuation-in-part of U.S. application Ser. No. 07/918,862, filed Jul. 30, 1992, now pending which was a continuation in part of U.S. application Ser. No. 07/746,381, filed Aug. 16, 1991, now abandoned and U.S. application Ser. No. 07/798,291, filed Nov. 26, 1991 now abandoned, the disclosures of each of which are incorporated herein by reference. This application is also a continuation-in-part of U.S. application Ser. No. 07/908,728, filed Jul. 6, 1992, now pending, which was a continuation of U.S. application Ser. No. 07/578,994, filed Sep. 6, 1990, now abandoned, which was a continuation-in-part of U.S. application Ser. No. 07/483,208, filed Feb. 20, 1990, now abandoned.

FIELD OF THE INVENTION

This invention relates to food formulations in which at least a portion of the fat and/or oil is replaced by a carbohydrate.

BACKGROUND OF THE INVENTION

U.S. Pat. No. 4,510,166 (Lenchin et al.) discloses converted starches having a DE less than 5 and certain paste and gel characteristics which are used as a fat and/or oil replacement in various foods, including ice cream and mayonnaise. The converted starches are described as dextrins, acid-converted starches (fluidity starches), enzyme-converted starches and oxidized starches. It is also disclosed that if the converted starches are not rendered cold-water soluble by the conversion, they are pregelatinized prior to use or cooked during use.

A product bulletin entitled "Paselli SA2; The Natural Alternative to Fats and Oils" (AVEBE b.a., Foxhol, Holland, Ref. No. 05.12.31.167 EF) discloses the use of a low-DE-hydrolysate (DE less than 3) made from potato starch as a replacement for fifty percent of the fat with an amount of the low-DE-potato starch hydrolysate plus water (starch hydrolysate at 28% dry solids) equal to the amount of fat replaced.

U.S. Pat. Nos. 3,962,465 (Richter et al.) and 3,986,890 (Richter et al.) disclose the use of thermoreversible gels of a starch hydrolysate (formed by enzymatic hydrolysis) as a substitute for fat in a variety of foods, including cake creams and fillings, mayonnaise and remoulades, cream cheeses and other cheese preparations, bread spreads, pastes, meat and sausage products, and whipped cream.

U.S. Pat. No. 4,971,723 (Chiu) discloses partially debranched starch prepared by enzymatic hydrolysis of the alpha-1,6-D-glucosidic bonds of the starch, comprising amylopectin, partially debranched amylopectin and up to 80% by weight, short amylose and that the partially debranched starch is useful in a variety of ways depending upon the degree of debranching. It is disclosed that a waxy maize starch (or other waxy starch) can be partially debranched (i.e. to 25% to 70% short chain amylose) to yield sufficient short chain amylose to form a thermally reversible Gel in an aqueous starch suspension. It is further disclosed that the same degree of debranching of waxy starches is preferred for lending a fat-like, lubricating texture to an aqueous starch dispersion.

SUMMARY OF THE INVENTION

This invention relates to method of making a composition of matter useful in replacing fat and/or oil in a food formulation comprising:

(a) gelatinizing a starch having an amylose component and an amylopectin component to form an aqueous mixture of amylose and amylopectin;

(b) exposing the aqueous mixture to a membrane that will allow an aqueous solution of essentially pure amylose to pass through said membrane, but will allow essentially no amylopectin to pass through said membrane;

(c) separating the amylopectin of said mixture from the amylose of said mixture by passing the amylose through said membrane with less than about 15% by weight of the dry solids through said membrane being amylopectin;

(d) precipitating said amylose from said aqueous solution;

(e) successively heating and then cooling said precipitated amylose while in contact with a major amount by weight of an aqueous medium to recrystallize at least a port/on of said precipitated amylose;

(f) fragmenting a minor amount of said dried precipitated and recrystallized amylose in a major amount of an aqueous liquid, said fragmenting being effective to form a particle gel of said composition.

In another aspect, this invention relates to a food formulation having a reduced level of fat and/or oil comprising a mixture of a foodstuff and a recrystallized and fragmented, precipitated amylose as a replacement for at least a substantial portion of the fat and/or oil of said food formulation, said recrystallized and fragmented, amylose precipitate being capable of forming a particle gel in aqueous dispersion.

In another aspect, this invention relates to a method of formulating a food containing a fat and/or oil ingredient comprising replacing at least a substantial portion of said fat and/or oil ingredient with a recrystallized and fragmented, amylose precipitate being capable of forming a particle gel in aqueous dispersion.

By "recrystallized and fragmented, amylose precipitate" is meant a starch material consisting essentially of amylose which has been subjected to precipitation followed by recrystallization and then mechanical disintegration of the precipitate into fragments. The disintegration will be sufficient to produce a precipitate which will form an aqueous dispersion having the characteristics of a particle gel.

In another aspect, this invention relates to a method of making a composition of matter useful in replacing fat and/or oil in a food formulation comprising physically fragmenting a minor amount of a recrystallized amylose precipitate in a major amount of an aqueous liquid, the degree of said physically fragmenting being sufficient to form a particle gel of said composition.

In another aspect, this invention relates to an aqueous dispersion useful as a replacement for fats and/or oils comprising a major amount by weight of water and a minor amount by weight of a recrystallized and fragmented amylose precipitate, the degree of fragmentation of said precipitate being sufficient to form a particle gel of said composition.

The terms "foodstuff" and "food", as used herein, are intended to broadly cover nutritional and/or functional materials that are ingested by humans in the course of consuming edible fare. The term "fats and/or oils" is intended to broadly cover edible lipids in general, specifically the fatty acid triglycerides commonly found in foods. The terms thus include solid fats, plastic shortenings, fluid oils, and the like. Common fatty acid triglycerides include cottonseed oil, soybean oil, corn oil, peanut oil, canola oil, sesame oil, palm oil, palm kernel oil, menhaden oil, whale oil, lard, and tallow. The technology of fats and/or oils is described generally by T. H. Applewhite, "Fats and Fatty Oils", *Encyclopedia of Chemical Technology*, Vol. 9, pp. 795–831 (Kirk-Othmer, eds., John Wiley & Sons, Inc., New York, New York, 3d ed., 1980), the disclosure of which is incorporated by reference.

The use of the terms "major" and "minor" in context together in this specification is meant to imply that the major component is present in a greater amount by weight than the minor component, and no more nor less should be inferred therefrom unless expressly noted otherwise in context.

DETAILED DESCRIPTION OF THE INVENTION

The recrystallized and fragmented amylose precipitate is made by the sequential steps of amylose purification, precipitation, recrystallization, and fragmentation of a starch material originally containing amylose and amylopectin. Starch is generally comprised of a highly-branched glucan having alpha-1,4 and alpha-1,6 linkages, denominated amylopectin, and a substantially linear glucan, having almost exclusively alpha-1,4 linkages, denominated amylose. Methods of determining the amounts of each are referenced in R. L. Whistler et al., *Starch: Chemistry and Technology*, pp. 25–35 (Academic Press, Inc., New York, N.Y., 1984), the disclosure of which is incorporated by reference. Common starches, i.e. starches having a substantial proportion (i.e. at least 20% by weight) of amylose are preferred for use in this invention because of their ready availability and examples of these include the common non-mutant starches of cereals, tubers and legumes, e.g. corn, wheat, rice, potato and tapioca, pea and mutant varieties comprised of a major proportion of amylose, e.g. high amylose corn starch. Common corn starch is a preferred example of the starches useful herein. However, starches containing a major amount of amylose (e.g. 50% to 75% by weight) are also useful and may be preferred depending upon the precise properties desired in the final product. Examples of such starches from high amylose corn include HI-SET $^R$ C and HYLON ™ (each about 55% amylose by weight) and HYLON ™ VII (about 70% amylose by weight), all available from National Starch and Chemical Corporation, Bridgewater, N.J.

If the starch chosen as a starting material is not in pre-gelatinized or instant form, the starch must be gelatinized or pasted prior to separation of the amylose and amylopectin. The gelatinization or pasting process disrupts, at least in substantial part, the associative bonding of the starch molecules in the starch granule. This permits the amylose and amylopectin to dissociate and disperse in an aqueous medium. This disruption is accomplished by heating a slurry of the starch to a sufficient temperature for a sufficient length of time depending upon the inherent resistance of the particular starch to gelatinization and the amount of moisture present in the slurry. The slurry will typically be comprised of a major amount of water (i.e. at least 50% by weight) and a minor amount of the starch starting material (i.e. less than about 50% by weight). Preferably, the starch slurry will contain at least about 5% starch, typically between about 10% to about 25% starch. The pH of the slurry will generally be substantially neutral, i.e. from about 3.5 to about 9 and more preferably from about 6 to 8, to minimize hydrolysis of the starch molecules. The time, temperature, slurry solids and pH should be optimized to gelatinize the starch, yet minimize hydrolysis of the starch.

The appropriate temperature, pressure and period of treatment needed to provide a starch paste is preferably obtained by processing aqueous starch slurries in equipment commonly known in the art as steam injection heaters or jet cookers. In such equipment, superatmospheric steam is injected and mixed with a water slurry of starch in a throat section of a jet. Upon contact with the injected steam, the starch granules are uniformly and thermally treated under turbulent conditions whereupon the starch granules are gelatinized and solubilized. Examples of steam injection heaters wherein the temperature, pressure and feed rate can be regulated to provide the desired starch pastes are disclosed in U.S. Pat. Nos 3,197,337; 3,219, 483 and 3,133,836. More uniformly solubilized starch pastes are obtained by use of the steam injection heater in combination with a holding zone such as coiled tubing or a pressurized tank constructed to minimize liquid channeling. Other pasting equipment, e.g. heat exchangers, homogenizers, cookers, votators, sizeometer cookers, kettle cookers, etc., may be employed provided the pasting conditions can be adequately maintained.

The gelatinized starch is then exposed to a membrane which is porous and has the proper pore size distribution to separate the amylose from the amylopectin in the solution to the degree desired. In general, the dry solids that pass through the membrane should contain less than 15% amylopectin on a dry weight basis, preferably less than 10%, more preferably less than 5% and most preferably less than 2% by weight amylopectin. Examples of particular means for obtaining such separation are disclosed in Japanese Patent Application No. 2-157077, filed Jun. 15, 1990, and laid open as JP-A-4-46901 on Feb. 17, 1992, and Japanese Patent Application No. 2-98823, filed Apr. 13, 1990, and laid open as JP-A-3-296501 on Dec. 27, 1991. The solution should not be allowed to cool for any substantial period of time which would allow a substantial proportion of the amylose to associate (e.g. retrograde) prior to exposure to the membrane. If the starch solution is allowed to cool, the amylose will not exist in a molecularly dispersed state that can pass through the membrane as a filtrate (or permeate).

The amylose filtrate is then optionally treated with a debranching enzyme, i.e. an enzyme capable of hydrolyzing the 1,6-glucosidic bond of amylopectin without significant capability of hydrolyzing the 1,4-glucosidic bond, to debranch any amylopectin that may have passed through the membrane. This treatment will not be necessary if the membrane has sufficient selectivity for amylose. Enzymes from a variety of sources are capable of debranching amylopectin. U.S. Pat. No. 3,370,840 (Sugimoto et al.) describes sources of debranching enzymes, the disclosure of which is incorporated herein by reference. Examples of useful enzymes include pullulanases derived from bacteria of the genus Aerobacter (e.g. E. C. 3.2.1.41 pullulan 6-glucanohydrolase) and isoamylases derived from bacteria of the genus Pseudomonas (e.g. E. C. 3.2.1.68 glycogen 6-glucanohydrolase). Particularly useful enzymes include thermostable enzymes, e.g. thermostable pullulanases as disclosed in PCT Publ. No. WO 92/02614, published Feb. 20, 1992, the disclosure of which is incorporated by reference, and which are obtained from members of the genus Pyrococcus. The debranching enzyme may be in solution during debranching or it may be immobilized on a solid support.

The debranching enzyme preparation should be as specific as possible for the hydrolysis of the 1,6-glucosidic bond of amylopectin and amylose. Thus, the enzyme preparation, if it contains a mixture of enzymes, is preferably essentially free of enzymes capable of hydrolyzing alpha-1,4-glucosidic bonds. Minimizing hydrolysis of alpha-1,4-glucosidic bonds will help to minimize the amounts of dextrose and soluble oligomers produced during debranching. Because these soluble saccharides are not believed to contribute to the functionality of the debranched material, minimizing their production will enhance the yield of functional material.

The debranching enzyme is allowed to act upon the amylose filtrate containing amylopectin. The optimum concentration of enzyme and substrate in the debranching medium will, in general, depend upon the level of activity of the enzyme which, in turn, will vary depending upon the enzyme source, enzyme supplier and the concentration of the enzyme in commercial batches. When the isoamylase E. C. 3.2.1.68, derived from Pseudomonas amyloderamosa, available from Sigma Chemical Co., St. Louis, Mo., is employed, typical conditions include the treatment of a starch solution at 5% to 30% by weight starch solids with about 50 units of enzyme per gram of starch for a period of about 48 hours to obtain substantially complete debranching.

The optimum pH and temperature of the debranching medium will also depend upon the choice of enzyme. The debranching medium may, in addition to the water used to solubilize the starch, contain buffers to ensure that the pH will be maintained at an optimum level throughout the debranching. Examples of useful buffers include acetates, citrates, and the salts of other weak acids. With the isoamylase described above, the pH is preferably maintained at about 4.0 to 5.0 and the temperature from about 40 degrees C. to about 50 degrees C. With the thermostable pullulanase described above, the pH is preferably maintained between 5 and 7 and the optimum temperature should be between 85 degrees C. and 115 degrees C.

The debranching is allowed to proceed until the desired degree of debranching has been obtained. The precise degree of debranching needed to obtain the desired ultimate particle gel of amylose particles may vary depending upon the source of the starch and the precise properties desired in the resulting gel. The degree of debranching should be sufficient to ensure that less than about 15% of the dry solids of the filtrate are amylopectin. In preferred embodiments, essentially all of the amylopectin is converted to short chain amylose. The amount of short chain amylose can be measured by gel permeation chromatography as set forth in U.S. Pat. No. 4,971,723, wherein the amylopectin appears as a broad peak eluting before the amylose.

After the desired degree of debranching is obtained, debranching enzyme in solution is deactivated, e.g. by heating to denature the enzyme. If an immobilized enzyme is employed, the contact time of the solubilized starch is adjusted so that the starch is removed from the enzyme when the desired degree of debranching is obtained. The amylose filtrate may be concentrated by removal of water therefrom, e.g. by evaporation, to facilitate precipitation. The amylose filtrate may also be treated to remove impurities therefrom. Treatment with, for example, activated carbon will remove residual proteins and lipids that may contribute to off-flavors and/or colors.

The solution of amylose is then allowed to form a precipitate. Generally, the solution will be cooled, e.g. to ambient temperature, to reduce the solubility of the amylose there. The solution will typically be allowed to stand until substantial equilibrium is achieved between the supernatant and the precipitate. The precipitate can be isolated from the supernatant, e.g. by centrifugation, prior to fragmentation, but isolation from the supernatant is not necessary to form a useful product.

Heating (e.g. to about 70 degrees C.) of the amylose precipitate while in contact with a liquid medium (e.g. the supernatant from original precipitation and/or fresh water following isolation of the precipitate from the supernatant) to dissolve at least a portion of the precipitate and then reprecipitation by cooling of the suspension/solution can also be employed. This reprecipitation tends to make the precipitate resistant to melting or dissolving when an aqueous dispersion of the fragmented precipitate is exposed to heat, e.g. in a pasteurization step. In general, the higher the temperature to which the precipitate in the liquid medium is heated (and thus the greater the amount of precipitate that is redissolved), the higher the temperature at which the resulting aqueous dispersion of fragmented precipitate will be stable. Repetition of the dissolving and reprecipitation also tends to improve the temperature stability of the resulting aqueous dispersion.

It is also advantageous to heat the precipitate to redissolve a substantial portion of the low melting polysaccharides and then treat the heated suspension of precipitate with acid or enzyme to hydrolyze soluble polysaccharides in the solution. (It may also be advantageous to filter the slurry while hot to remove soluble polysaccharides or their hydrolysates.) The dissolving and reprecipitation steps alone improve the stability of the aqueous dispersion by increasing the amount of the fragmented precipitate which remains as insoluble fragments in an aqueous dispersion that is exposed to heat.

After precipitation, the precipitate is recrystallized. This is accomplished by slowly heating and then cooling the precipitate. The term recrystallized does not denote solubilzation of amylose, but merely a reordering of the crystalline and/or any amorphous phases to a more stable crystalline state. This slow rate of heating and/or cooling will typically be at a rate of from about 0.005 degrees C./min. to about 1.0 degrees C./min. for each and over a temperature range of about 50 degrees C. to 100 degrees C. This recrystallization will make the precipitate much more stable (i.e. resisitant to solubilization) at elevated tempertures.

However, any remaining soluble fraction of the precipitate can associate to form relatively large particles that are present in the precipitate after fragmentation and that can contribute a "chalky" or "gritty" texture to the dispersion. Treatment of the heated suspension/solution of the precipitate with acid or enzyme to hydrolyze a substantial portion of the soluble fraction can reduce or eliminate such large particles. Typical treatment conditions will involve mild hydrolysis catalyzed by acid, e.g. in a solution of 0.1 N HCl for one hour, or, preferably, by enzyme, e.g. alpha-amylase.

The isolated amylose precipitate is typically washed and then dried (e.g. to a low moisture content, typically 3-8%) after isolation to allow for handling and storage prior to further processing. Examples of drying techniques include spray drying, flash drying, tray drying, belt drying, and sonic drying. The dried precipitate may be hygroscopic. Thus, some rehydration during handling and storage may occur. Depending upon the precise composition of the precipitate and the conditions (including length of time) of storage, steps to maintain the moisture at a low content may be necessary (e.g. moisture barrier packaging and/or control of humidity in the storage environment). If the moisture content is allowed to rise too far (e.g. greater than about 20%, or possibly greater than 15%), bulk handling problems and/or microbiological stability problems might arise.

The amylose precipitate may also be otherwise chemically modified. Examples of such chemical modification include the product of reaction with bleaching agents (e.g. hydrogen peroxide, peracetic acid, ammonium persulfate, chlorine (e.g. calcium and/or sodium hypochlorite or sodium chlorite), and permanganate (e.g. potassium permanganate)); esterifying agents (e.g. acetic anhydride, adipic anhydride, octenyl succinic anhydrides, succinic anhydride, vinyl acetate); including phosphorous compounds (e.g. monosodium orthophosphate, phosphorous oxychloride, sodium tripolyphosphate, and sodium trimetaphosphate); and/or etherifying agents (e.g. acrolein, epichlorohydrin, and/or propylene oxide). Such chemical modifications will typically be accomplished after the precipitation step, but may be accomplished prior to the precipitation or effected by using a modified starch as a starting material for the gelatinization step, provided such modification does not preclude efficient precipiation.

The amylose precipitate is subjected to a physical fragmentation as by mechanical disintegration, i.e. fragmented. The degree of fragmentation will be sufficient to allow the precipitate to form a particle gel in an aqueous medium. Certain steps can be taken prior to fragmentation to enhance the susceptibility of the precipitate to fragmentation. For example, the addition to the solution of additives which will introduce imperfections into the crystalline structure of the precipitate, e.g. higher saccharides such as maltodextrins, may make the precipitate easier to fragment to the desired degree. Subjecting a slurry of the precipitate to mild hydrolysis catalyzed by acid, e.g. in a solution of 0.1 N HCl for one hour, or, preferably, by enzyme, e.g. alpha-amylase, may also make fragmentation easier.

The mechanical disintegration of the precipitate may be carried out in several ways, as by subjecting it to attrition in a mill, or to a high speed shearing action, or to the action of high pressures. Disintegration is generally carried out in the presence of a major amount by weight of a liquid medium, preferably water. Although tap water is the preferred liquid medium for the dispersion of fragmented amylose precipitate, other liquids are suitable provided sufficient water is present to hydrate the fragmented amylose precipitate and, thus, result in a dispersion having the characteristics of a particle gel. Sugar solutions, polyols, of which glycerol is an example, alcohols, particularly ethanol, isopropanol, and the like, are good examples of suitable liquids that can be in admixture with water in the liquid medium. It may also be possible to fragment the amylose precipitate in a non-hydrating medium (e.g. 95% ethanol), then solvent exchange with water, and finally redisperse the fragmented amylose precipitate to form an aqueous dispersion. Typically, however, the amylose precipitate will be physically fragmented in potable water.

The mechanical disintegration is preferably accomplished by subjecting an aqueous dispersion of the precipitate to high shear, e.g. in a Waring blender or a homogenizer such as that disclosed in U.S. Pat. No. 4,533,254 (Cook et al.) and commercially available as a MICROFLUIDIZER TM from Microfluidics Corporation, Newton, Mass., or a homogenizer such as the RANNIE TM high pressure laboratory homogenizer, Model Mini-lab, type 8.30 H, APV Rannie, Minneapolis, Minn. Homogenizers useful in forming suspensions or emulsions are described generally by H. Reuter, "Homogenization", *Encyclopedia of Food Science*, pp. 374–376, (M. S. Peterson and A. H. Johnson, eds., AVI Publ. Co., Westport, Conn., 1978), L. H. Rees and W. D. Pandolfe, "Homogenizers" *Encyclopedia of Food Engineering*, pp. 467–472 (C. W. Hall et al., eds., AVI Publ. Co., Westport, Conn., 1986), and W. C. Griffin, "Emulsions" *Encyclopedia of Chemical Technology*, Vol. 8, pp. 900–930 (Kirk-Othmer, eds., John Wiley & Sons, Inc., New York, N.Y., 3d ed., 1979), the disclosures of which are incorporated herein by reference.

The temperature of the amylose precipitate during the fragmentation step should be maintained below the temperature at which a major portion of the precipitate will dissolve in the aqueous medium. Thus, it may be desirable to cool the precipitate during disintegration. However, the amylose precipitate should be quite stable to elevated temperatures and, thus, cooling during fragmentation should not be necessary. Whatever method is used, the disintegration is carried out to such an extent that the resulting finely-divided product is characterized by its ability to form a particle gel in the liquid medium in which it is attrited or in which it is subsequently dispersed.

The recrystallized and fragmented amylose particles which make up the particle gel can be analyzed in a variety of ways. Rheological measurements can be made to determine the rheological characteristics of the resulting dispersion. Typically, the aqueous dispersion of debranched amylopectin starch particles will exhibit a transition in dynamic elastic modulus (G') versus shear strain at less than about 50 millistrain, and preferably less than about 10 mlllistrain, said transition being from a substantially constant G' versus shear strain to a decreasing G' versus shear strain. The transition indicates fracture of the particle network within the particle gel and is typically a sharp transition. Analysis of the amylose particles by X-ray diffraction will show that the material has a measurable crystallinity. Such measurements are well within the skill of those in this art.

It should also be noted that mechanical disintegration may be sufficient to produce an aqueous dispersion having the desired particle gel characteristics, but still leave a sufficient number of particles of sufficient size to exhibit a "particulate" or "chalky" mouthfeel when ingested. Such chalkiness can be reduced by the mild hydrolysis discussed above or by reducing the particle size of the starch precipitate before, during or after mechanical disintegration so that substantially all (typically at least about 95%, preferably at least 99%) of the precipitate will pass a U.S. #325 mesh sieve (i.e. substantially all particles are less than 45 microns). An example of a milling device suitable for such size reduction is a TROST ™ Air Impact Mill from Garlock, Inc., Newton, Pa.

The use of the recrystallized and fragmented, amylose precipitate allows for the replacement of a substantial portion (e.g. from 10% to 100% by weight) of the fat and/or oil in a food formulation. The precise level of replacement that is possible without significantly decreasing the organoleptic quality of the food will generally vary with the type of food. For example, in a French-style salad dressing, it is generally possible to completely replace the oil component that is normally present. In other types of foods, e.g. frostings, icings, cream fillings, ice cream, margarine, etc., a major amount of the fat and/or oil (e.g. about 50% to about 80%) can be replaced with little effect on the organoleptic desirability of the food. Examples of typical foods in which fat and/or oil can be replaced include frostings (e.g. icings, glazes, etc. ), creme fillings, frozen desserts (e.g. ice milk, sherbets, etc.), dressings (e.g. pourable or spoonable salad and/or sandwich dressings), meat products (e.g. sausages, processed meats, etc.), cheese products (e.g. cheese spreads, processed cheese foods), margarine, fruit butters, other imitation dairy products, puddings (e.g. mousse desserts), candy (e.g. chocolates, nougats, etc.), and sauces, toppings, syrups and so on.

Generally, it will be desirable to remove sufficient fat from a given food formulation to achieve a reduction in calories of at least one-third per customary serving or make a label claim of "cholesterol-free". (In this regard, see, for example, the list of standard serving sizes for various foods published in Food Labelling; Serving Sizes, 55 Fed. Reg. 29517 (1990) (to be codified at 21 C.F.R. 101.12), the disclosure of which is incorporated herein by reference, and the restrictions on labelling "cholesterol-free" at Food Labelling; Definitions of the Terms Cholesterol Free, Low Cholesterol and Reduced Cholesterol, 55 Fed. Reg. 29456 (1990)). It should also be noted that the fat removed from a particular formulation may be replaced with an equal amount by weight of an aqueous dispersion of fragmented starch precipitate, but that such equality may not be necessary or desirable in all instances. Further, it may be desirable to remove fat and add another ingredient (e.g. a gum, polydextrose, a protein, etc.) along with the aqueous dispersion of starch precipitate.

While this invention is generally directed to the replacement of fat and/or oil in a food formulation, it is of course within the contemplation of this invention that a recrystallized and fragmented amylose precipitate will be used in an entirely new formulation to which it contributes fat-like organoleptic qualities but is not, in the strictest sense, replacing a pre-existing fat or oil ingredient. Moreover, it is contemplated that the amylose precipitate will have utility as a thickener, bodying agent, or the like in foods that normally do not have a significant fat or oil component.

In general, the recrystallized and fragmented amylose precipitate is incorporated into the food as an aqueous dispersion, typically comprised of a major amount (i.e. greater than 50% by weight) of water or other liquid medium and a minor amount (i.e. less than 50% by weight, typically 10% to 40%) of starch precipitate solids. Alternatively, the isolated precipitate can be mixed with the food along with water and then subjected to disintegration in those instances when the other ingredients of the food are capable of withstanding the condition of disintegration, e.g. a salad dressing or imitation sour cream.

It is contemplated that commercial production and use may involve hydrolysis, mechanical disintegration, and drying (e.g. spray drying) of the recrystallized and fragmented amylose precipitate to produce an item of commerce. This item of commerce will then be purchased by a food processor for use as an ingredient. To incorporate the dried, fragmented, amylose precipitate into a food product, it may be useful and/or necessary to further mechanically disintegrate the amylose precipitate while dispersing it into the foodstuff in which it will be employed. However, the techniques employed for such mechanical disintegration should not need to be nearly as vigorous as the original mechanical disintegration prior to drying.

As noted above, the terms "food" and "foodstuffs" are intended broadly, as relating to both nutritional and/or functional food ingredients. It is contemplated that one or more food ingredients may be mixed with the aqueous dispersion of recrystallized and fragmented amylose precipitate, or even dry mixed with the precipitate prior to mechanical disintegration.

Among the food ingredients in the food formulations of this invention include flavors, thickeners (e.g. starches and hydrophilic colloids), nutrients (e.g. carbohydrates, proteins, lipids, etc.), antioxidants, antimicrobial agents, non-fat milk solids, egg solids, acidulants, and so on. Hydrophilic colloids can include natural gum material such as xanthan gum, gum tragacanth, locust bean gum, guar gum, algin, alginates, gelatin, Irish moss, pectin, gum arabic, gum ghatti, gum karaya and plant hemicelluloses, e.g. corn hull gum. Synthetic gums such as water-soluble salts of carboxymethyl cellulose can also be used. Starches can also be added to the food. Examples of suitable starches include corn, waxy maize, wheat, rice, potato, and tapioca starches.

Non-fat milk solids which can be used in the compositions of this invention are the solids of skim milk and include proteins, mineral matter and milk sugar. Other proteins such as casein, sodium caseinate, calcium caseinate, modified casein, sweet dairy whey, modified whey, and whey protein concentrate can also be used herein.

For many foods, it is accepted practice for the user to add the required amount of eggs in the course of preparation and this practice may be followed just as well herein. If desired, however, the inclusion of egg solids, in particular, egg albumen and dried yolk, in the food are allowable alternatives. Soy isolates may also be used herein in place of the egg albumen.

Dry or liquid flavoring agents may be added to the formulation. These include cocoa, vanilla, chocolate, coconut, peppermint, pineapple, cherry, nuts, spices, salts, flavor enhancers, among others.

Acidulants commonly added to foods include lactic acid, citric acid, tartaric acid, malic acid, acetic acid, phosphoric acid, and hydrochloric acid.

Generally, the other components of the various types of food formulations will be conventional, although precise amounts of individual components and the presence of some of the conventional components may well be unconventional in a given formulation. For example, the conventional other components for foods such as frozen desserts and dressings, are described in European Patent Publication No. 0 340 035, published Nov. 2, 1989 (the pertinent disclosure of which is incorporated herein by reference), and the components and processing of table spreads is disclosed in U.S. Pat. No. 4,869,919 (Lowery), the disclosure of which is incorporated by reference.

A particularly advantageous use of the fragmented amylose precipitate described herein may be the use thereof to replace a portion of the shortening used in a layered pastry article. In layered pastry articles (Danish, croissants, etc.) layers of a bread dough are assembled with a "roll-in" placed between the layers. The roll-in commonly contains a "shortening" (i.e. a fat and/or oil component) from an animal (e.g. butter) or vegetable (e.g. partially hydrogenated soybean oil) source. The assembled article, optionally containing a filling or topping, is then baked to form a finished pastry. At least a portion of the shortening of an otherwise conventional roll-in can be replaced with an aqueous dispersion of the fragmented amylose precipitate, preferably in admixture with an emulsifier (e.g. mono- and/or di-glycerides), and used to make a layered pastry.

The following examples will illustrate the invention and variations thereof within the scope and spirit of the invention will be apparent therefrom. All parts, percentages, ratios and the like are by weight throughout this specification and the appended claims, unless otherwise noted in context.

EXAMPLES

Example 1

Regular corn starch is mixed with water to prepare about a 20% solids slurry. The slurry is adjusted to pH 7 then jet cooked at about 320 degrees F. and held at that temperature for at least about 2 minutes. The resulting hot starch paste is then diluted with water to about 10% solids and filtered through a filtration membrane, at about 190 degrees F., having an average pore diameter of 0.01 to 0.1 micrometers as described in Japanese Patent Application 4-46901.

The resulting filtrate containing the amylose fraction is concentrated to about 20% solids and optionally debranched using a pullulanase or isoamylase enzyme. The concentrated amylose solution is allowed to cool to about room temperature with agitation to form a precipitated/semi-crystalline slurry.

The resulting amylose slurry is heated to 50 degrees C. and then heated to 100 degrees C. at the rate of 0.05 degrees C./minute, then cooled to 50 degrees C. at the rate of 0.05 degrees C./minute. The resulting slurry is treated with sufficient hydrochloric acid to give a final salt content after neutralization of 1.5% to the final product. The acid is added and the temperature adjusted to 140 degrees F. to about 190 degrees F. and the reaction mass agitated at the temperature for a time sufficient to render the acid treated product easily shearable and impart a creamy texture on shearing, but not so long as to create a substantial amount of soluble saccharides that contribute nothing to yield stress. The final product is desired to have a yield stress value of at least about 400 pascals for a 20% solids creme after shearing.

The product after acid treatment is adjusted to pH 4.5 and optionally microfiltered to remove soluble saccharides. The product slurry is then spray dried to give less than 8% moisture content.

The resulting dry product is then reslurried by a customer at about 20% solids and sheared using a shearing device such as a Microfluidizer at 8000 psi and with an exit temperature of 140 degrees F. The creme at 20% solids has a yield stress value at 400 pascals or greater.

Example 2

The resulting spray-dried powder of the precipitate from above is prepared as a 30% d.s. creme for use in making a reduced fat sour cream. The creme preparation involves making a 30% d.s. slurry of the precipitate and heating it to 75 degrees C. The hot slurry is sheared in a MICROFLUIDIZER using module 1351 and 15,000 psi. The resulting creme is incorporated into the following reduced fat sour cream formula:

| Ingredients: | % |
| --- | --- |
| Precipitate (30% d.s. creme) | 39.79 |
| Sour cream | 29.83 |
| Water | 23.41 |
| Non-fat dry milk | 5.97 |
| Lactic acid 88% | 0.40 |
| Xanthan gum | 0.20 |
| Salt | 0.20 |
| Sodium citrate | 0.20 |

Procedure

Lactic acid is added to the water and mixed well with a Kitchen A/de mixer. The dry ingredients are added and incorporated into the water making a slurry. The precipitate dispersion and the sour cream are blended into the slurry. The resulting material is hand homogenized and refrigerated.

What is claimed is:

1. A method of making a composition of matter useful in replacing fat and/or oil in a food formulation comprising:
   (a) gelatinizing a starch having an amylose component and an amylopectin component to form an aqueous mixture of amylose and amylopectin;
   (b) exposing the aqueous mixture to a membrane that will allow an aqueous solution of essentially pure amylose to pass through said membrane, but will allow essentially no amylopectin to pass through said membrane;
   (c) separating the amylopectin of said mixture from the amylose of said mixture by passing the amylose through said membrane with less than about 15% by weight of the dry solids through said membrane being amylopectin;
   (d) precipitating said amylose from said aqueous solution;
   (e) successively heating and then cooling said precipitated amylose while in contact with a major amount by weight of an aqueous medium to recrystallize at least a portion of said precipitated amylose; and
   (f) fragmenting by mechanical disintegration a minor amount of said precipitated and recrystallized amylose in a major amount of an aqueous liquid, said fragmenting being effective to form a particle gel of said composition.

2. A method of claim 1 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

3. A method of claim 1 wherein said starch is derived from a variety of Zea mays.

4. A method of claim 1 wherein said starch is derived from a variety of Zea mays having less than about 40% by weight amylose.

5. A method of claim 1 wherein the dry solids of the solution passing through said membrane contain less than 5% by weight amylopectin.

6. A method of claim 1 wherein less than 80% by weight of said fragmented amylose precipitate will dissolve in water at 100 degrees C. when dispersed therein at 2% solids of fragmented amylose precipitate.

7. A method of claim 1 wherein said fragmented amylose precipitate is essentially free of amylopectin.

* * * * *